(12) United States Patent
DeLuca et al.

(10) Patent No.: US 6,579,861 B2
(45) Date of Patent: Jun. 17, 2003

(54) 1α-HYDROXY-2-METHYLENE-19-NOR-HOMOPREGNACALCIFEROL AND ITS USES

(75) Inventors: Hector F. DeLuca, Deerfield, WI (US); Rafal R. Sicinski, Warsaw (PL); Sumithra Gowlugari, Madison, WI (US); Lori A. Plum, Madison, WI (US); Margaret Clagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/165,123

(22) Filed: Jun. 7, 2002

(65) Prior Publication Data

US 2002/0183289 A1 Dec. 5, 2002

Related U.S. Application Data

(60) Division of application No. 09/878,438, filed on Jun. 11, 2001, now Pat. No. 6,440,953, which is a continuation-in-part of application No. 09/657,828, filed on Sep. 8, 2000, now abandoned.

(51) Int. Cl.$^7$ .......................... A61K 31/59; C07C 40/00
(52) U.S. Cl. ........................................ 514/167; 552/653
(58) Field of Search ........................... 514/167; 552/653

(56) References Cited

U.S. PATENT DOCUMENTS

| | | | |
|---|---|---|---|
| 4,666,634 A | 5/1987 | Miyamoto et al. | 260/397.2 |
| 4,800,198 A | 1/1989 | DeLuca et al. | 514/167 |
| 5,089,641 A | 2/1992 | DeLuca et al. | 552/653 |
| 5,536,713 A | 7/1996 | Deluca et al. | 514/167 |
| 5,578,587 A | 11/1996 | DeLuca et al. | 514/167 |
| 5,587,497 A | 12/1996 | DeLuca et al. | 552/653 |
| 5,817,648 A | * 10/1998 | Kutner et al. | 514/167 |
| 5,840,718 A | * 11/1998 | Hennessy et al. | 514/167 |
| 5,843,928 A | 12/1998 | Deluca et al. | 514/167 |
| 5,877,168 A | 3/1999 | Miyamoto et al. | 514/167 |
| 5,936,133 A | 8/1999 | Deluca et al. | 568/828 |
| 5,945,410 A | 8/1999 | DeLuca et al. | 514/167 |

OTHER PUBLICATIONS

Brown et al, "New Active Analogues of Vitamin D with Low Calcemic Activity" Kidney International, vol. 38, Suppl. 29 (1990) pp. S–22–S–27.

Hareau et al, "Asymmetric Synthesis of $1_\alpha,25$–Dihydroxyvitamin $D_3$ A–Ring Precursor Starting with 5–Tert–Butyldimethylsiloxy–2–Cyclohexenone" Tetrahedron Letters, 41 (2000) pp. 2385–2388.

Sicinski et al, "New $1_\alpha,25$–Dihydroxy–19–Norvitamin $D_3$ Compounds of High Biological Activity: Synthesis and Biological Evaluation of 2–Hydroxymethyl, 2–Methyl, and 2–Methylene Analogues" J. Med. Chem., 41 (1998) pp. 4662–4674.

* cited by examiner

*Primary Examiner*—Sabiha Qazi
(74) *Attorney, Agent, or Firm*—Andrus, Sceales, Starke & Sawall, LLP

(57) ABSTRACT

This invention discloses 1α-hydroxy-2-methylene-19-nor-homopregnacalciferol and pharmaceutical uses therefor. This compound exhibits pronounced activity in arresting the proliferation of undifferentiated cells and inducing their differentiation to the monocyte thus evidencing use as an anti-cancer agent and for the treatment of skin diseases such as psoriasis as well as skin conditions such as wrinkles, slack skin, dry skin and insufficient sebum secretion. This compound also has little, if any, calcemic activity and therefore may be used to treat immune disorders in humans as well as renal osteodystrophy.

7 Claims, 7 Drawing Sheets

1α-HYDROXY-2-METHYLENE-19-NOR-HOMOPREGNACALCIFEROL AND ITS USES

CROSS REFERENCE TO RELATED APPLICATION

This application is a divisional of U.S. patent application Ser. No. 09/878,438 filed Jun. 11, 2001, now U.S. Pat. No. 6,440,953, which in turn is a continuation-in-part of U.S. patent application Ser. No. 09/657,828 filed Sep. 8, 2000, now abandoned.

BACKGROUND OF THE INVENTION

This invention relates to vitamin D compounds, and more particularly to 1α-hydroxy-2-methylene-19-nor-homopregnacalciferol and its pharmaceutical uses.

The natural hormone, 1α,25-dihydroxyvitamin $D_3$ and its analog in ergosterol series, i.e. 1α,25-dihydroxyvitamin $D_2$ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases as renal osteodystrophy, vitamin D-resistant rickets, osteoporosis, psoriasis, and certain malignancies.

Recently, a new class of vitamin D analogs has been discovered, i.e. the so called 19-nor-vitamin D compounds, which are characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

Recently, 2-substituted analogs of 1α,25-dihydroxy-19-nor-vitamin $D_3$ have also been synthesized, i.e. compounds substituted at 2-position with hydroxy or alkoxy groups (DeLuca et al., U.S. Pat. No. 5,536,713), with 2-alkyl groups (DeLuca et al U.S. Pat. No. 5,945,410), and with 2-alkylidene groups (DeLuca et al U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, an analog which is characterized by the presence of a methylene substituent at the carbon 2 (C-2) has been synthesized and tested. Of particular interest is the analog which is characterized by a hydroxyl group at carbon 1 and a shortened side chain attached to carbon 20, i.e. 1α-hydroxy-2-methylene-19-nor-homopregnacalciferol. This vitamin D analogs seemed an interesting target because the relatively small methylene group at C-2 should not interfere with the vitamin D receptor. Moreover, molecular mechanics studies performed on the model 1α-hydroxy-2-methylene-19-nor-vitamins indicate that such molecular modification does not change substantially the conformation of the cyclohexanediol ring A. However, introduction of the 2-methylene group into 19-nor-vitamin D carbon skeleton changes the character of its 1α- and 3β-A-ring hydroxyls. They are both now in the allylic positions, similarly, as 1α-hydroxyl group (crucial for biological activity) in the molecule of the natural hormone, 1α,25-$(OH)_2D_3$.

SUMMARY OF THE INVENTION

The present invention is directed toward 1α-hydroxy-2-methylene-19-nor-homopregnacalciferol, its biological activity, and various pharmaceutical uses for this compound.

Structurally this 19-nor analog is characterized by the general formula I shown below:

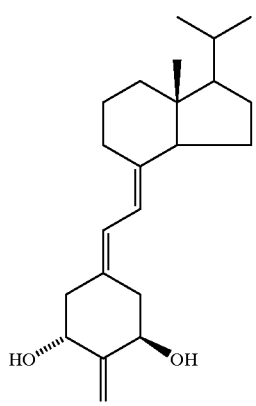

I

The above compound exhibits a desired, and highly advantageous, pattern of biological activity. This compound is characterized by relatively high binding to vitamin D receptors, but very low intestinal calcium transport activity, as compared to that of 1α,25-dihydroxyvitamin $D_3$, and has very low ability to mobilize calcium from bone, as compared to 1α,25-dihydroxyvitamin $D_3$. Hence, this compound can be characterized as having little, if any, calcemic activity. However, its apparent ability to also suppress production of parathyroid hormone (PTH) makes this compound an ideal candidate for use as a therapeutic agent for the treatment of renal osteodystrophy.

The compound of the invention has also been discovered to be especially suited for treatment and prophylaxis of human disorders which are characterized by an imbalance in the immune system, e.g. in autoimmune diseases, including multiple sclerosis, lupis, diabetes mellitus, host versus graft reaction, and rejection of organ transplants; and additionally for the treatment of inflammatory diseases, such as rheumatoid arthritis, asthma, and inflammatory bowel diseases such as celiac disease and croans disease, as well as the improvement of bone fracture healing and improved bone grafts. Acne, alopecia and hypertension are other conditions which may be treated with the compound of the invention.

The above compound is also characterized by relatively high cell differentiation activity. Thus, this compound also provides a therapeutic agent for the treatment of psoriasis, or as an anti-cancer agent, especially against leukemia, colon cancer, breast cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin.

The compound may be present in a composition to treat the above-noted diseases and disorders in an amount from about 0.01 μg/gm to about 100 μg/gm of the composition, and may be administered topically, transdermally, orally or parenterally in dosages of from about 0.01 μg/day to about 100 μg/day.

DETAILED DESCRIPTION OF THE INVENTION

1α-hydroxy-2-methylene-19-nor-homopregnacalciferol (referred to herein as 2 MHP) was synthesized and tested. Structurally, this 19-nor analog is characterized by the general formula I previously illustrated herein.

The preparation of 1α-hydroxy-2-methylene-19-nor-homopregnacalciferol having the basic structure I can be accomplished by a common general method, i.e. the condensation of a bicyclic Windaus-Grundmann type ketone 11 with the allylic phosphine oxide III to the corresponding 2-methylene-19-nor-vitamin D analog IV followed by deprotection at C-1 and C-3 in the latter compound:

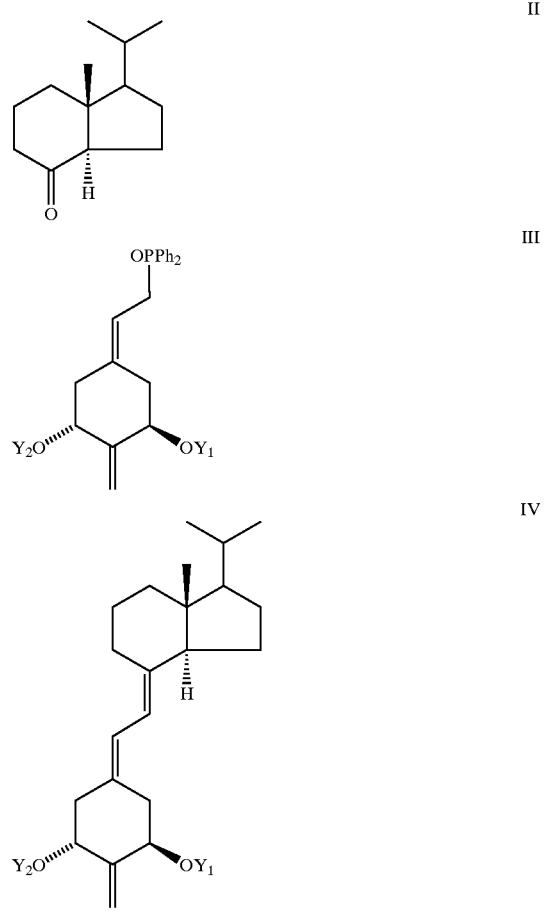

In the structures II, III, and IV groups $Y_1$ and $Y_2$ are hydroxy-protecting groups, it being also understood that any functionalities that might be sensitive, or that interfere with the condensation reaction, be suitably protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

Hydrindanones of the general structure 11 are known, or can be prepared by known methods.

For the preparation of the required phosphine oxides of general structure III, a new synthetic route has been developed starting from a methyl quinicate derivative which is easily obtained from commercial (1R,3R,4S,5R)-(−)-quinic acid as described by Perlman et al., Tetrahedron Lett. 32, 7663 (1991) and DeLuca et al., U.S. Pat. No. 5,086,191.

The overall process of the synthesis of compound I is illustrated and described more completely in U.S. application Ser. No. 09/370,966 filed Aug. 10, 1999 entitled "2-Alkylidene-19-Nor-Vitamin D Compounds" the specification of which is specifically incorporated herein by reference.

Biological Activity of 1α-Hydroxy-2-Methylene-
19-nor-Homopregnacalciferol

Figure 1:
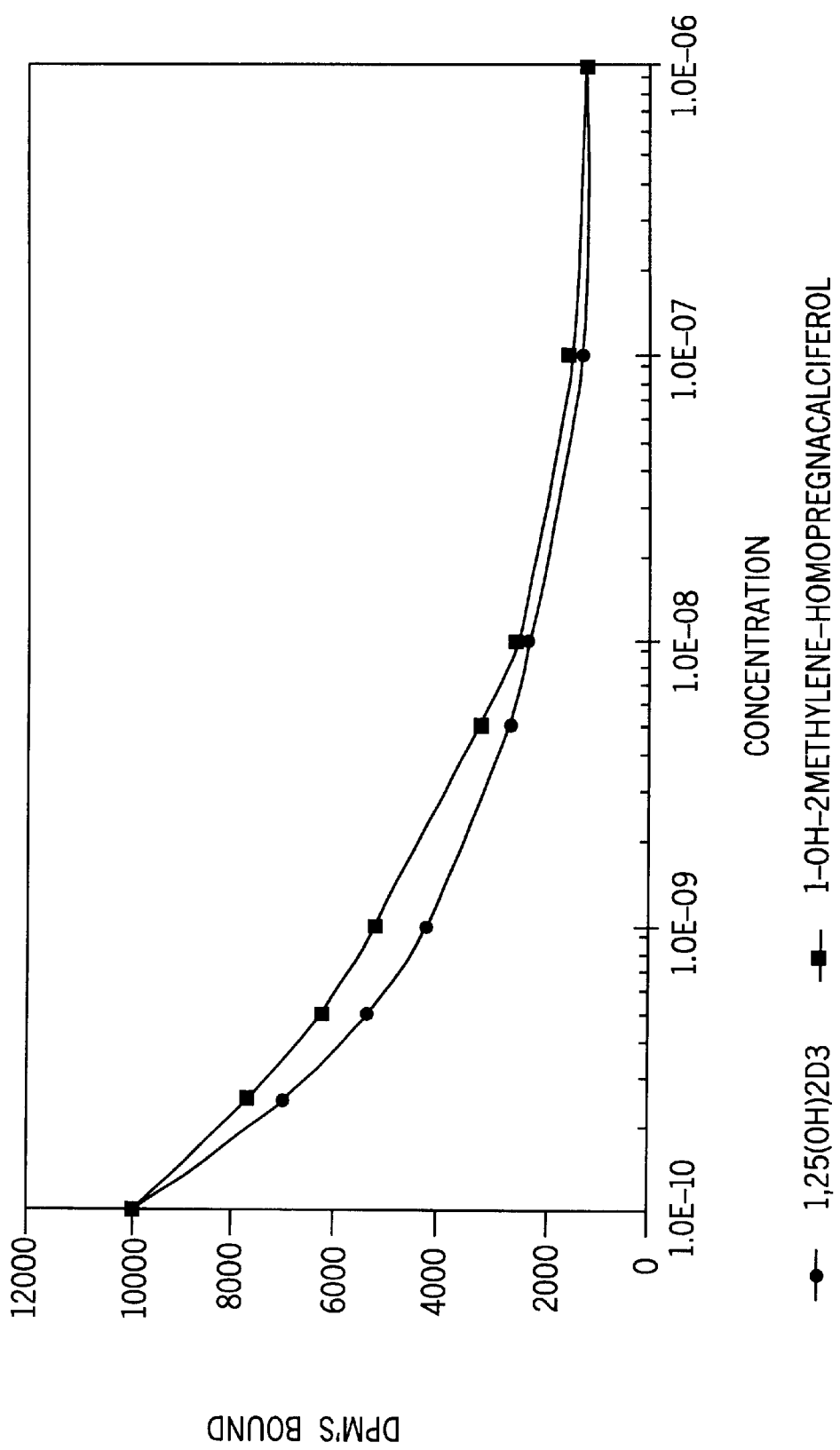
FIG. 1 is a graph illustrating the relative activity of 1α-hydroxy-2-methylene-19-nor-homopregnacalciferol and 1α,25-dihydroxyvitamin $D_3$ to compete for binding of [$^3$H]-1,25-$(OH)_2$-$D_3$ to the vitamin D pig intestinal nuclear receptor.

The introduction of a methylene group to the 2-position of 1α-hydroxy-19-nor-homopregnacalciferol had little or no effect on binding to the porcine intestinal vitamin D receptor, as compared to 1α,25-dihydroxyvitamin $D_3$. This compound bound equally well to the porcine receptor as compared to the standard 1,25-$(OH)_2D_3$ (FIG. 1). It might be expected from these results that this compound would have equivalent biological activity. Surprisingly, however, the 2 methylene substitution produced a highly selective analog with unique biological activity.

Figure 2:
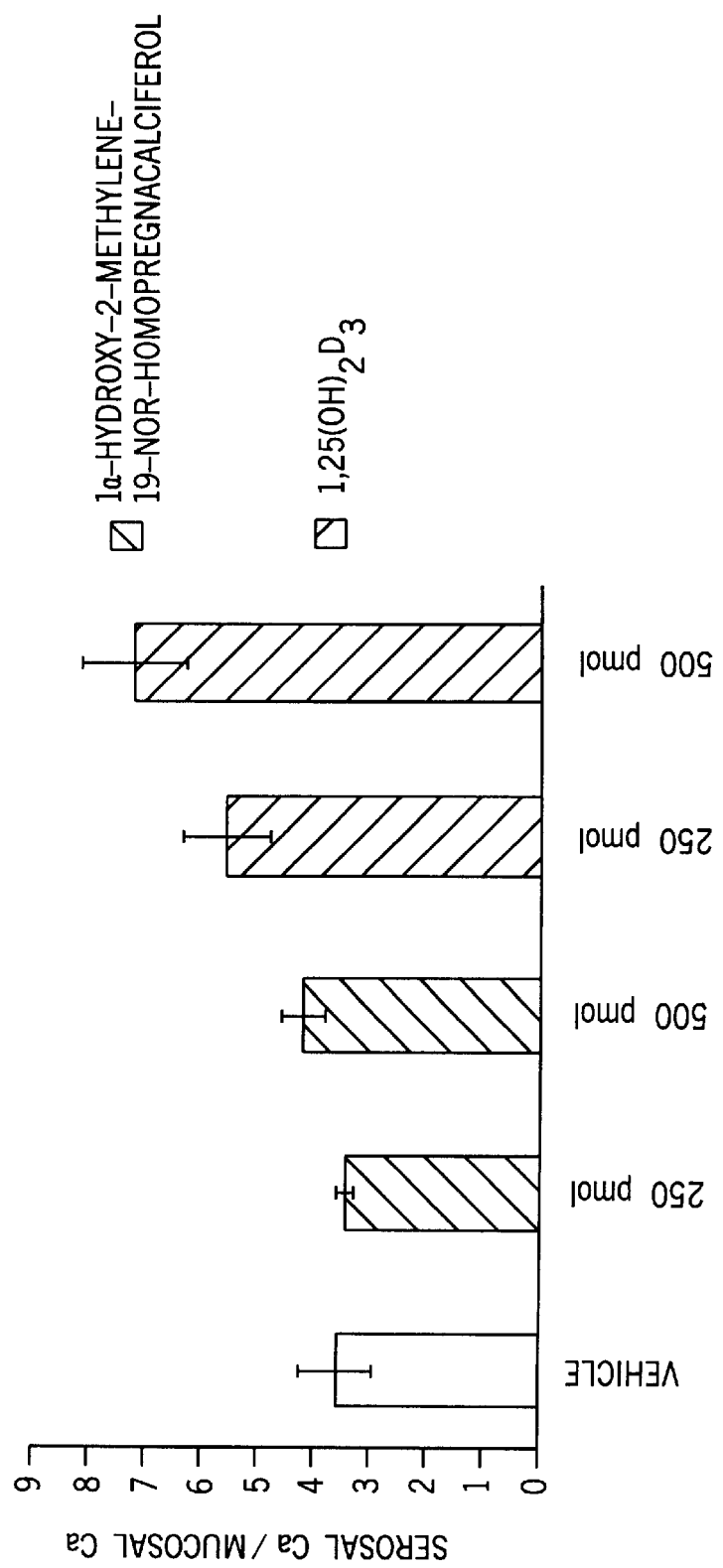
FIG. 2 is a graph illustrating the intestinal calcium transport activity of 1α-hydroxy-2-methylene-19-nor-homopregnacalciferol as compared to 1α,25-dihydroxyvitamin $D_3$.

Table 1 and FIG. 2 show that 2 MHP has very little activity as compared to that of 1,25-dihydroxyvitamin $D_3$ (1,25$(OH)_2D_3$), the natural hormone, in stimulating intestinal calcium transport.

Figure 3:
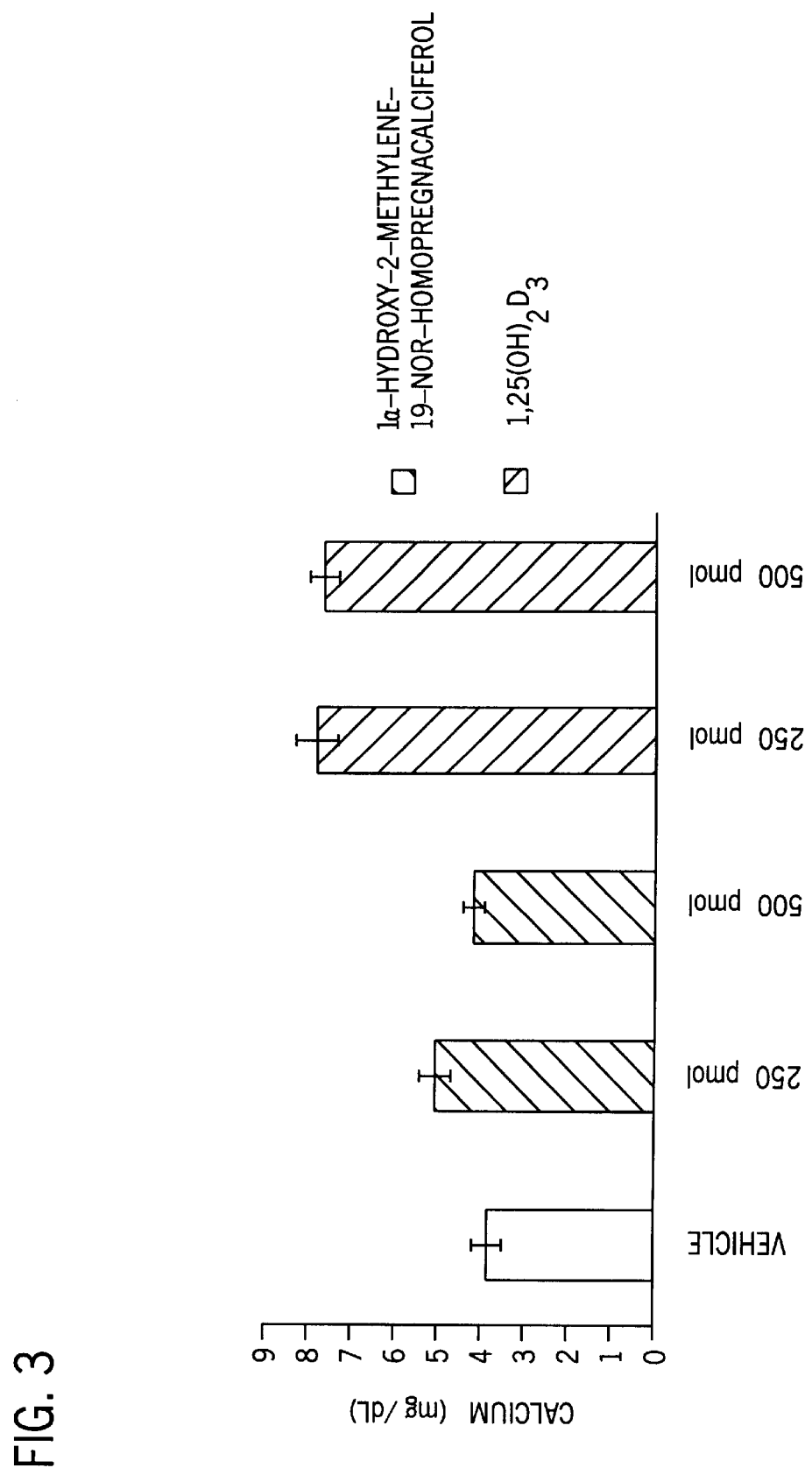
FIG. 3 is a graph illustrating the bone calcium mobilization activity of 1α-hydroxy-2-methylene-19-nor-homopregnacalciferol as compared to 1α,25-dihydroxyvitamin $D_3$.

Table 1 and FIG. 3 demonstrate that 2 MHP has very little bone calcium mobilization activity, as compared to 1,25 $(OH)_2D_3$.

FIGS. 2 and 3 thus illustrate that 2 MHP may be characterized as having little, if any, calcemic activity.

Figure 4:
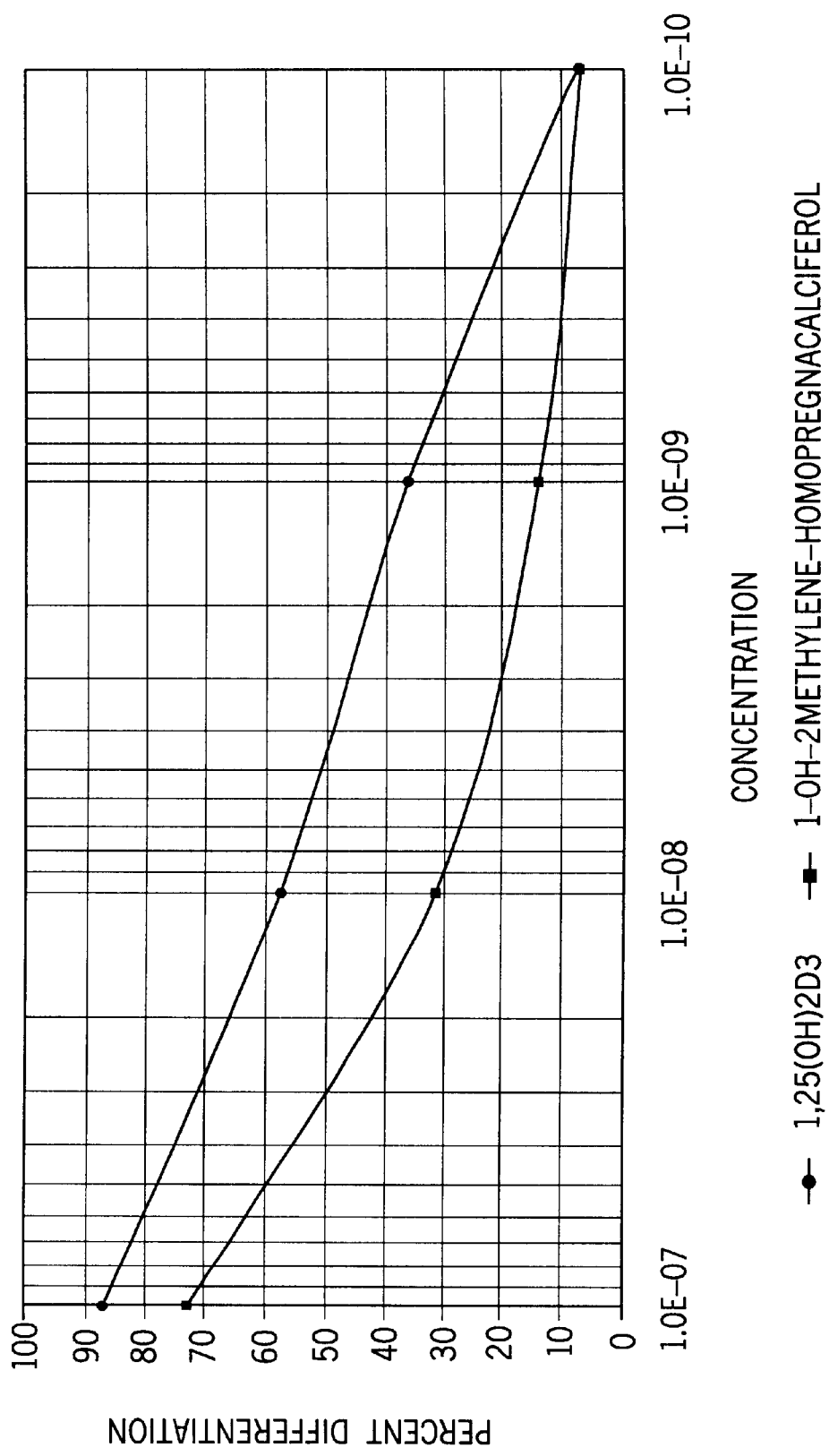
FIG. 4 is a graph illustrating the percent HL-60 cell differentiation as a function of the concentration of 1α-hydroxy-2-methylene-19-nor-homopregnacalciferol and of 1α,25-dihydroxyvitamin $D_3$.

FIG. 4 illustrates that 2 MHP is almost as potent as 1,25$(OH)_2D_3$ on HL-60 differentiation, making it an excellent candidate for the treatment of psoriasis and cancer, especially against leukemia, colon cancer, breast cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin.

Figure 5:
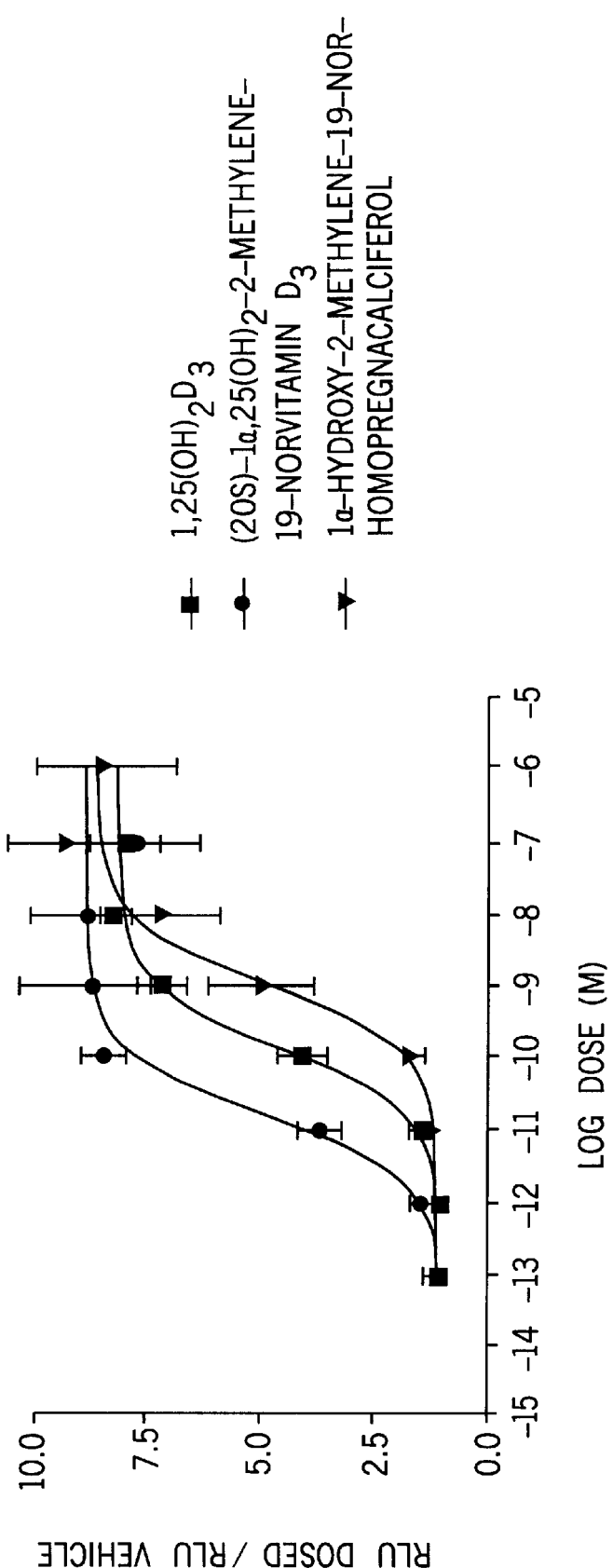
FIG. 5 is a graph illustrating the transcriptional activity in bone cells of 1α-hydroxy-2-methylene-19-nor-homopregnacalciferol as compared to 2-methylene-19-nor-20(S)-1α,25-dihydroxyvitamin $D_3$ and to 1α,25-dihydroxyvitamin $D_3$.
Figure 6:
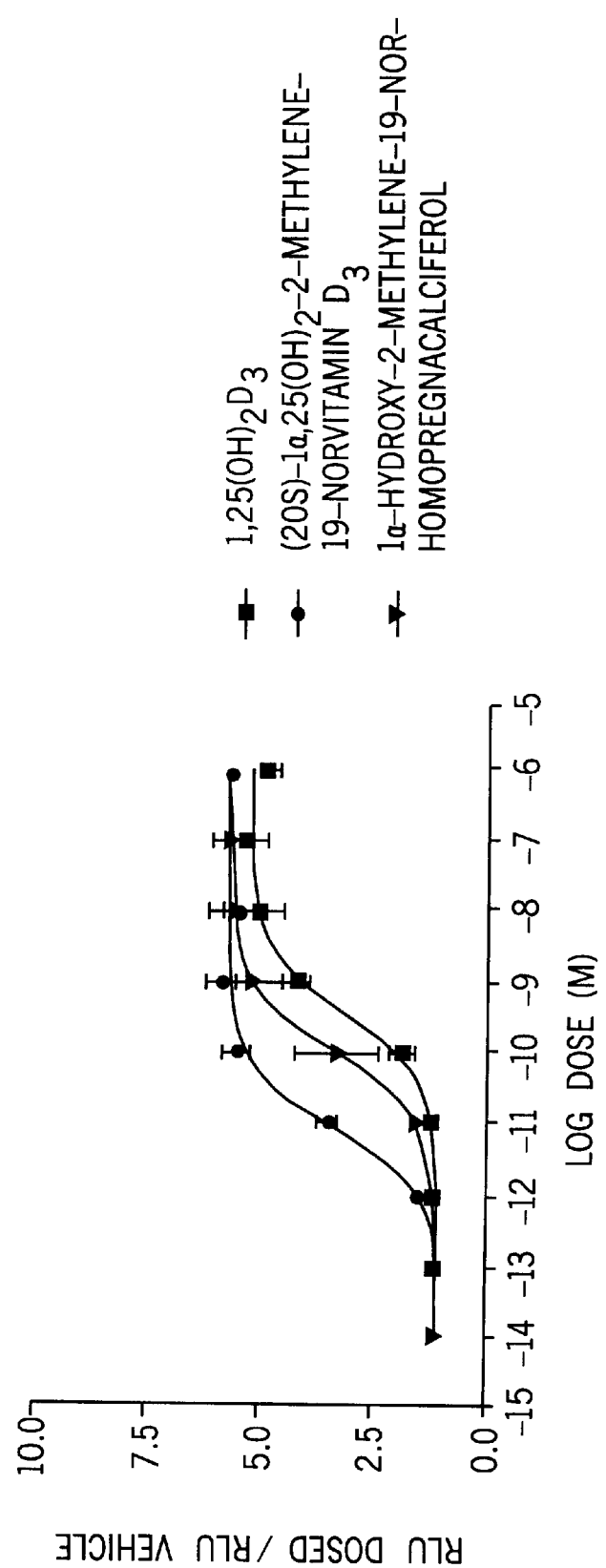
FIG. 6 is a graph illustrating the transcriptional activity in kidney cells of 1α-hydroxy-2-methylene-19-nor-homopregnacalciferol as compared to 2-methylene-19-nor-20(S)-1α,25-dihydroxyvitamin $D_3$ and to 1α,25-dihydroxyvitamin $D_3$.

FIG. 5 illustrates that 2 MHP has transcriptional activity in bone cells while FIG. 6 illustrates 2 MHP has transcriptional activity in kidney cells. These data provide further support for the VDR binding data in FIG. 1. Transcriptional activity was measured in two different cell lines. ROS 17/2.8 (bone) or LLC (kidney) cells were stably transfected with a 24-hydroxylase (24OHase) gene promoter upstream of a luciferase reporter gene (Arbour et al, 1998). Cells were given a range of doses. Sixteen hours after dosing the cells were harvested and luciferase activities were measured using a luminometer. The $EC_{50}$ of 1α-hydroxy-2-methylene-19-nor-homopregnacalciferol is about 10 times lower in bone cells than kidney cells. In kidney cells, 1α-hydroxy-2-methylene-19-nor-homopregnacalciferol is greater than or equivalent to 1,25$(OH)_2D_3$. The graphs of FIGS. 5 and 6 are representative of 4 to 5 independent experiments. In FIGS. 5 and 6, RLU means relative luciferase units.

Figure 7:
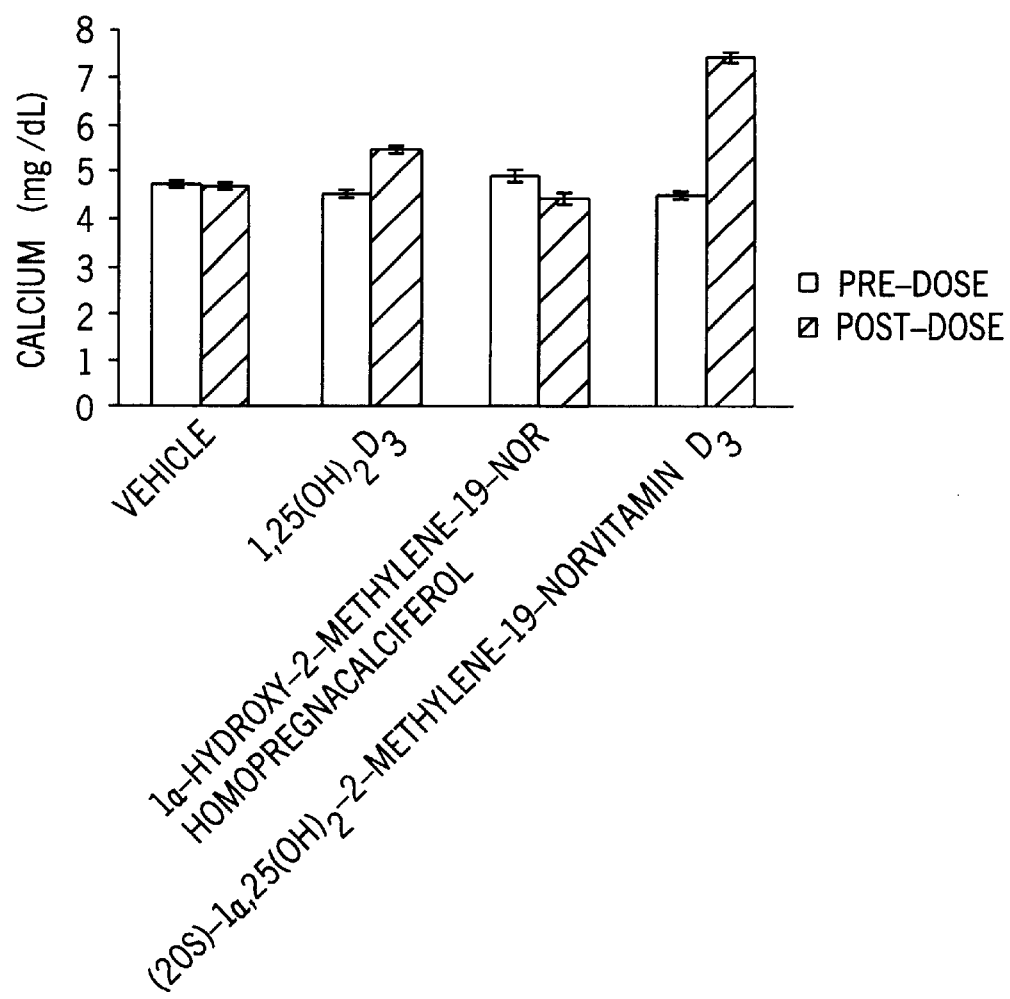
FIG. 7 is a bar graph illustrating blood serum calcium levels in male rats after treatment with a single dose of 1α-hydroxy-2-methylene-19-nor-homopregnacalciferol as compared to 1α,25-dihydroxyvitamin $D_3$ and to 2-methylene-19-nor-20(S)-1α,25-dihydroxyvitamin $D_3$.

Table 2 and FIG. 7 show an analysis of serum calcium in rats both before and after administration of a single dose of 2 MHP. These data provide further support for the data in FIG. 3.

Competitive binding of the analogs to the porcine intestinal receptor was carried out by the method described by Dame et al (Biochemistry 25, 4523–4534, 1986).

The differentiation of HL-60 promyelocytic into monocytes was determined as described by Ostrem et al (J. Biol. Chem. 262, 14164–14171, 1987).

Interpretation of Data

The in vivo tests to determine serum calcium of rats on a zero calcium diet provides an insight to osteoblastic or bone activity of 2 MHP. The dose response curves show that 2 MHP is significantly less potent than 1,25$(OH)_2D_3$ in raising calcium in the plasma via the stimulation of the osteoblasts (FIG. 3 and FIG. 7). At the same time, the activity of 2 MHP on intestinal calcium transport is also significantly less than that of 1,25-$(OH)_2D_3$ (FIG. 2). Therefore, these data show 2 MHP to have little, if any, activity on bone. 2 MHP is slightly less active than 1,25$(OH)_2D_3$ in binding to the vitamin D receptor (FIG. 1), and has significant transcriptional activity in both bone cells (FIG. 5) and kidney cells (FIG. 6). However, it is also only slightly less active than 1,25-$(OH)_2D_3$ in causing differentiation of the promyelocyte, HL-60, into the monocyte (FIG. 4). This result suggests that 2 MHP will be very effective in psoriasis because it has direct cellular activity in causing cell differentiation and in suppressing cell growth. It also indicates that it will have significant activity as an anti-cancer agent, especially against leukemia, colon cancer, breast cancer and prostate cancer, as well as against skin conditions such as dry skin (lack of dermal hydration), undue skin slackness (insufficient skin firmness), insufficient sebum secretion and wrinkles.

These results illustrate that 2 MHP is an excellent candidate for numerous human therapies and that it may be useful in a number of circumstances such as autoimmune diseases, cancer, and psoriasis. Since 2 MHP has significant binding activity to the vitamin D receptor, but has little ability to raise blood serum calcium, and yet has the ability to suppress PTH production, it may also be useful for the treatment of renal osteodystrophy.

Male, weanling Sprague-Dawley rats were placed on Diet 11 (0.47% Ca) diet+AEK for 11 days, followed by Diet 11 (0.02% Ca)+AEK for 31 days. Dosing (i.p.) began 7 days prior to sacrifice. Doses were given on a daily basis, 24 hours apart. The first 10 cm of the intestine was collected for gut transport studies and serum was collected for bone Ca mobilization analysis. The results are reported in Table 1 and illustrated in the graph of FIG. 2.

TABLE 1

Response of Intestinal Calcium Transport and Serum Calcium (Bone Calcium Mobilization) Activity to Chronic Doses of 1,25$(OH)_2D_3$ and 2MHP

| Group | Dose (pmol/day/7 days) | Intestinal Calcium Transport* (S/M) | Serum Calcium* (mg/100 ml) |
|---|---|---|---|
| Vitamin D Deficient | Vehicle | 3.28 ± 0.64 | 3.72 ± 0.32 |
| 1,25-$(OH)_2D_3$ | 250 | 5.21 ± 0.73 | 7.40 ± 0.47 |
| 1,25-$(OH)_2D_3$ | 500 | 6.85 ± 0.79 | 7.20 ± 0.33 |
| 2MHP | 250 | 3.22 ± 0.14 | 4.84 ± 0.37 |
| 2MHP | 500 | 3.90 ± 0.38 | 3.96 ± 0.19 |

*The above data are the average and standard error (SE) from 5 animals.

Weanling, male Sprague-Dawley rats (6/group) were placed on a vitamin D-deficient diet for a total of 5 weeks. During the first three weeks, the animals were fed a normal calcium diet (Diet 11+0.47% Ca+AEK supplement) and the last two weeks they were fed a low calcium diet (Diet 11+0.02% Ca+AEK supplement). Approximately 24 hours prior to sacrifice, animals were tail bled and then dosed with 1 nmol of the respective compounds. The doses were delivered orally in 100 microliters of vegetable oil by gavage. Serum was collected approximately 24 hour post-dose and it, along with the pre-dose serum, were subjected to total calcium analysis using atomic absorption spectrometry. These data are reported below in Table 2 and illustrated in the graph of FIG. 7.

TABLE 2

Pre-Dose and Post-Dose Response of Serum Calcium (Bone Mobilization) Activity to a Single Dose of $1,25(OH)_2D_3$ and of 2MHP and of 2-Methylene-19-Nor-20(S)-$1,25(OH)_2D_3$

| Treatment | Pre-Dose* | SE | Post-Dose* | SE |
|---|---|---|---|---|
| Vehicle | 4.70 | 0.08 | 4.64 | 0.12 |
| $1,25(OH)_2D_3$ | 4.51 | 0.05 | 5.42 | 0.09 |
| 1α-hydroxy-2-methylene-19-nor-homopregnacalciferol | 4.86 | 0.13 | 4.36 | 0.16 |
| (20S)-1α,25(OH)$_2$-2-methylene-19-nor-vitamin D$_3$ | 4.45 | 0.06 | 7.33 | 0.15 |

*The above are the average and standard error (SE) from 6 animals.

For treatment purposes, the compound of this invention defined by formula I may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compound may be administered orally, topically, parenterally or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. Doses of from 0.01 μg to 100 μg per day of the compounds are appropriate for treatment purposes, such doses being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin D$_2$ or D$_3$, or 1α,25-dihydroxyvitamin D$_3$—in situations where different degrees of bone mineral mobilization and calcium transport stimulation is found to be advantageous.

Compositions for use in the above-mentioned treatments comprise an effective amount of the 1α-hydroxy-2-methylene-19-nor-homopregnacalciferol as defined by the above formula I as the active ingredient, and a suitable carrier. An effective amount of such compound for use in accordance with this invention is from about 0.01 μg to about 100 g per gm of composition, and may be administered topically, transdermally, orally or parenterally in dosages of from about 0.01 μg/day to about 100 μg/day.

The compound may be formulated as creams, lotions, ointments, topical patches, pills, capsules or tablets, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compound is advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For asthma treatment, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A method of treating psoriasis comprising administering to a patient with psoriasis an effective amount of 1α-hydroxy-2-methylene-19-nor-homopregnacalciferol having the formula:

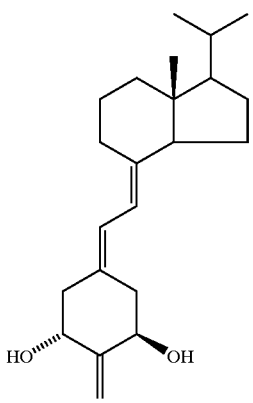

2. The method of claim 1 wherein 1α-hydroxy-2-methylene-19-nor-homopregnacalciferol is administered orally.

3. The method of claim 1 wherein 1α-hydroxy-2-methylene-19-nor-homopregnacalciferol is administered parenterally.

4. The method of claim 1 wherein 1α-hydroxy-2-methylene-19-nor-homopregnacalciferol is administered transdermally.

5. The method of claim 1 wherein 1α-hydroxy-2-methylene-19-nor-homopregnacalciferol is administered topically.

6. The method of claim 1 wherein 1α-hydroxy-2-methylene-19-nor-homopregnacalciferol is administered in a dosage of from about 0.01 μg/day to about 100 μg/day.

7. 1α-hydroxy-2-methylene-19-nor-homopregnacalciferol having the formula:

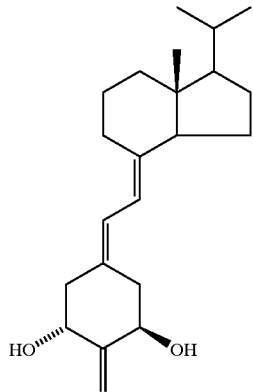

* * * * *